United States Patent [19]

Michalowicz

[11] 4,024,187

[45] * May 17, 1977

[54] PREPARATION OF M-AMINO-α-METHYLBENZYL ALCOHOL

[75] Inventor: William Michalowicz, Lock Haven, Pa.

[73] Assignee: American Color & Chemical Corporation, Charlotte, N.C.

[ * ] Notice: The portion of the term of this patent subsequent to May 3, 1994, has been disclaimed.

[22] Filed: May 24, 1974

[21] Appl. No.: 473,230

[52] U.S. Cl. .............................. 260/580; 260/575
[51] Int. Cl.$^2$ ........................................ C07C 85/11
[58] Field of Search ........................... 260/580, 575

[56] References Cited

UNITED STATES PATENTS

| 2,683,745 | 7/1954 | Emerson et al. | 260/580 X |
|---|---|---|---|
| 2,797,244 | 6/1957 | Tinsley | 260/580 |
| 3,032,586 | 5/1962 | Dierichs et al. | 260/580 |
| 3,154,584 | 10/1964 | Gardner et al. | 260/580 |
| 3,423,462 | 1/1969 | Rylander | 260/580 |
| 3,499,034 | 3/1970 | Gonzalez | 260/580 |

OTHER PUBLICATIONS

House, Modern Synthetic Reactions, W. A. Benjamin, Inc. California, 2nd ed. pp. 1–8 (1972).

*Primary Examiner*—Helen M. S. Sneed
*Attorney, Agent, or Firm*—Armstrong, Nikaido & Marmelstein

[57] ABSTRACT m-Amino-α-methylbenzyl alcohol is produced in a facile manner in a single step hydrogenation from m-nitroacetophenone under relatively mild conditions with standard hydrogenation catalysts through the utilization of an aqueous reaction medium.

6 Claims, No Drawings

PREPARATION OF M-AMINO-α-METHYLBENZYL ALCOHOL

BACKGROUND OF THE INVENTION

In the preparation of dyestuffs, m-amino-α-methylbenzyl alcohol is a useful intermediate which can be readily introduced into chromophoric molecules to produce useful dyestuffs. For example m-amino-α-methylbenzyl alcohol may be condensed with haloanthraquinones to yield arylaminoanthraquinones which, when devoid of water solubilizing groups such as sulfo and carboxy, find utility in the field of polyester dyestuffs. In spite of the fact that such end product anthraquinones would be good dyestuff, their use has been somewhat restricted by the difficulty of obtaining the necessary starting material, m-amino-α-methylbenzyl alcohol, in a facile, inexpensive manner. Various researchers have reported on new ways for the synthesis of m-amino-α-methylbenzyl alcohol, but for the reasons set forth hereinbelow there are numerous drawbacks to such methods.

There are numerous reports in the literature of the hydrogenation of m-nitroacetophenone under a relatively low hydrogen pressure such as 2–5 atmospheres in various solvents using the common hydrogenation catalysts such as nickel, palladium and platinum. Reports of such research are found in *Chemical Abstracts*, 46, 10180i; 47, 5380e; 55, 25795e; *J. Am. Chem. Soc.*, 68, 1088; and British Pat. No. 1,104,168. Such methods suffer from drawbacks, however, in that the second stage hydrogenation of the intermediate m-aminoacetophenone to the desired m-amino-α-methylbenzyl alcohol is reported only under extreme conditions such as 2000 psi to 4700 psi at 120° C to 155° C, as reported in British Pat. No. 758,993 and U.S. Pat. No. 2,608,136. Thus, the prior art method requiring a two-step hydrogenation and the use of very extreme conditions in the second stage represents a distinct drawback to the worker of ordinary skill in the art, faced with the problem of producing economical intermediate products for the synthesis of dyestuffs.

In British Pat. No. 758,993 there is described a proposal for the one-step catalytic preparation of m-amino-α-methylbenzyl alcohol from m-nitroacetophenone, but a pressure of 2000 psi at 120° C is required, Raney nickel being used in a dioxane solvent. A two stage process is discussed in U.S. Pat. No. 2,608,136 where m-nitroacetophenone is first catalytically reduced to m-amino-acetophenone under mild conditions which utilizes Raney nickel. However, the second stage requires the use of high pressure on the order of 4700 to 4800 psi with a copper chromite catalyst at a temperature of in excess of 150° C.

From the foregoing, it is seen that most of the prior art processes discussed herein require a two stage treatment. Furthermore, the prior art processes teach the conversion of the starting or intermediate material to m-amino-α-methylbenzyl alcohol only under extreme conditions of pressure.

SUMMARY OF THE INVENTION

In accordance with the invention, a facile one-step preparation of m-amino-α-methylbenzyl alcohol from m-nitroacetophenone is disclosed. m-Amino-α-methylbenzyl alcohol is produced by a process for the facile conversion of m-nitroacetophenone into a m-amino-α-methylbenzyl alcohol in a single step process which comprises treating m-nitroacetophenone in an aqueous medium with hydrogen, said hydrogen being under a pressure of from about 25 to about 1000 psi in the presence of from about 1 to about 40 parts per 100 parts of m-nitroacetophenone of a conventional nickel or palladium catalyst; the reaction being conducted at a temperature below about 105° C.

DETAILED DESCRIPTION OF THE INVENTION

In carrying out the invention, it is important that an aqueous medium be utilized. If other media are substituted for the aqueous medium of the invention, such as an alcohol, dioxane, or the like, it has been found that the reaction may stop at the intermediate stage of the m-aminoacetophenone. Therefore, in carrying out the invention, an aqueous medium is critical.

Nickel or a palladium catalysts provide optimum results. The catalysts are used in their commercially available form and as used herein the parts of catalyst, unless otherwise specified, refer to the parts of catalyst in their commercially available form. Thus, for example, the parts of nickel catalysts used herein refer to parts of commercially available nickel catalysts in the form of aqueous slurries containing generally 45 to 50% by weight of the catalyst. For these catalysts, therefore, the amount of catalyst in terms of metal is from about 0.4 parts to about 20 parts per 100 parts of m-nitroacetophenone. The palladium catalysts on the other hand are generally available as 5% palladium-on-carbon catalysts. Thus the amount of palladium, per se, useful in the present invention is in the range of about 0.05 to .25 parts per 100 parts of m-nitroacetophenone. Smaller amounts of the catalysts may be used but the rate of reaction is too slow to be commercially attractive. The use of larger amounts of catalysts are not economically justified.

A temperature of just below 100° C has been found suitable for the reaction, with a range of about 75° C to 105° C being particularly suitable. Care must be exercised to control the temperature as too high a temperature will destroy the excellent yield and purity of the product obtained in accordance with the invention. A temperature of 120° C has been found to produce unacceptable results.

The time of the reaction will become apparent to the worker skilled in the art and will be influenced by the pressure which is found desirable in carrying out the reaction. Generally, a time of from about 3 to 5 hours is suitable.

Although one of the advantages of the present invention is that a relatively low pressure may be used, operable pressures vary within a wide range of from 25 to 1000 psi. A pressure of from about 90 to about 110 psi, however, is preferred.

The concentration in the aqueous medium of the starting material, m-nitroacetophenone, may be any amount up to about 1.66 moles per liter of water. If the concentration of m-nitroacetophenone exceeds 1.66 moles per liter of water in the charge to the autoclave the hydrogenation will stop short of completion to the desired product with m-aminoacetophenone as the other product.

With the nickel catalyst, if very pure m-nitroacetophenone is used (i.e., 100% by GLC as obtained, for example, by crystallization from ethanol) the hydrogenation will not occur or will occur slowly. Where crude (less than 100% purity) m-nitroacetophenone is used the impurities present being acidic sulfuric acid, nitric acid, or other acid material contained in the m-nitroacetophenone as obtained directly from the nitration of acetophenone without further purification-the process is operable. Crude m-nitroacetophenone when suspended in water gives a strongly acid system with a pH of 2.6 to 3.2. If very pure m-nitroacetophenone is used and fails to hydrogenate, the addition of a few drops of sulfuric acid to the aqueous suspension will permit hydrogenation to occur to yield the desired product.

The palladium catalyst, however, requires pure (100% by GLC as obtained, for example, by crystallization from ethanol) m-nitroacetophenone. The impurities present in crude m-nitroacetophenone adversely affect the palladium catalyst.

The following examples serve to further illustrate the invention:

EXAMPLE I m-Nitroacetophenone [123.8 g., 0.75 mole, 99% purity by gas-liquid chromatography (GLC)], water (450 ml.) and Raney nickel catalyst (40 g. (wet) Grace No. 4200) was charged to a 1 liter Parr stirring autoclave. The reaction mass was stirred at 100 psi constant hydrogen pressure while the temperature was adjusted slowly to 99° C (the exotherm of hydrogenation contributed initially to the temperature increase from ambient, 26° C). After 4 hours there was no further evidence of hydrogen absorption. The hydrogenate was filtered at 60°–70° C and the clear, light amber colored filtrate was cooled to 10° C with stirring. After stirring one hour, the original filtrate was again filtered to give 54.5 g. of m-amino-$\alpha$-methylbenzyl alcohol (53.0% yield). which was 100% pure by GLC. The filtrate was evaporated under vacuum to leave a residue of 42.1 g. which was 100% m-amino-$\alpha$-methylbenzyl alcohol by GLC. Total yield of 96.6 g. (94.0% yield).

EXAMPLE II

Following the procedure of Example I m-nitroacetophenone (82.5 g., 0.50 mole; 99% purity by GLC), water (300 ml.), and Raney nickel catalyst (27 g. (wet), Grace No. 4200) charged to a 1 liter Parr stirring autoclave. The hydrogen pressure was 50 psi initially and allowed to decrease to 40 psi whereupon the pressure was raised to 50 psi and again allowed to decrease as hydrogenation continued. The temperature was slowly raised from 25° C to 100° C. After 6½ hours, hydrogen absorption apparently ceased. Work-up as in example I gave 26.5 g. m-amino-$\alpha$-methylbenzyl alcohol (38.7% yield) which was 100% pure by GLC and a residue of 38.1 g. which contained 87.2% m-amino-$\alpha$-methylbenzyl alcohol and 12.8% m-aminoacetophenone.

EXAMPLE III

Following the procedure of Example I there was charged m-nitroacetophenone (33.0 g. 0.20 mole, 99% purity), water (300 ml.), and Raney nickel (14.8 g. (wet), Grace No. 4200) under 300 psi to 250 psi hydrogen. After 2½ hours, work-up, by complete evaporation of the filtered hydrogenate, yielded 26.7 g. (97% yield) of m-amino-$\alpha$-methylbenzyl alcohol which was 99.3% pure by GLC.

EXAMPLE IV

The procedure of Example I was followed. m-Nitroacetophenone (99.0 g. 0.60 mole, 99% GLC), water (400 ml.), and Raney Nickel-Chromium catalyst (35 g. (wet), Grace No. 24) was charged to a 1 liter Parr stirring autoclave. The reaction mass was maintained under 100 psi constant hydrogen pressure at 95° C to 97° C until hydrogen absorption ceased (3⅔ hours). The filtered hydrogenate was stirred for one hour at 10° C to 15° C and filtered. The product obtained after vacuum drying (20.7 g., 25%) was 100% m-amino-$\alpha$-methylbenzyl alcohol by GLC analysis. The filtrate was evaporated under vacuum to leave a residue of 56.1 g. (68%) which gave the following analysis by GLC:
m-ethylaniline — 0.2%
unknown — 2.7%
m-amino-$\alpha$-methylbenzyl alcohol — 95.6%
m-aminoacetophenone — 1.5%

EXAMPLE V

Same procedure and charge as in Example IV except that Harshaw nickel catalyst 0104P (25 g.) was used. Hydrogen absorption ceased after 5 hours at 94° to 99° C at 100 psi constant hydrogen pressure. Evaporation of the hydrogenate under vacuum gave a residue of 76.2 g. (92%) which gave the following analysis by GLC:
m-amino-$\alpha$-methylbenzyl alcohol — 98.4%
m-ethylaniline — 0.7%
m-aminoacetophenone — 0.9%

Example VI

Same procedure and charge as in Example IV except that Girdler nickel catalyst G-69 (20 g.) was used. After 6 hours at 99° C to 101° C under 100 psi constant pressure, the hydrogenation was terminated although slow hydrogen absorption was still observed. Analysis of the evaporated filtered hydrogenate gave the following analysis by GLC:
m-amino-$\alpha$-methylbenzyl alcohol — 95.5%
m-aminoacetophenone — 4.5%

EXAMPLE VII m-Nitroacetophenone (99.0 g., 0.60 mole, 100% by GLC), water (400 ml.), and (Engelhard) 5% Palladium on carbon (2.0 g.) were charged to a 1 liter Parr stirring autoclave. The reaction mass was hydrogenated at 100 psi constant hydrogen pressure at 91° C to 99° C until hydrogen absorption ceased (2 5/6 hours). Evaporation of the filtered hydrogenate gave 78.7 g. of residue (95.7%) which by GLC analysis was 100% m-amino-$\alpha$-methylbenzyl alcohol.

EXAMPLE VIII

Following the procedure of Example I there was charged m-nitroacetophenone (123.8 g., 0.75 mole, 99% purity), water (450 ml.), and 40 g. Raney nickel catalyst (wet). Work-up by filtration gave 53.5 g. of m-amino-$\alpha$-methylbenzyl alcohol. The filtrate was charged with m-nitroacetophenone (66.0 g., 0.40 mole) and hydrogenated with the same catalyst until absorption ceased under 100 psi as in Example I. Work-up by filtration gave 54.6 g., 0.40 mole, of m-amino-$\alpha$-methylbenzyl alcohol equivalent to the moles of m-nitroacetophenone charged in the first recycle.

EXAMPLE IX

Same charge and catalyst as in Example I except that the hydrogenation temperature was 115° C to 120° C at 100 psi hydrogen pressure. After 5 hours, the reaction was terminated even though hydrogen absorption was still occurring. Analysis of the product by GLC indicated 43% m-amino-α-methylbenzyl alcohol and 57% m-ethylaniline.

What is claimed is:

1. A process for the facile conversion of m-nitroacetophenone into m-amino-α-methylbenzyl alcohol in a single step process comprising hydrogenating m-nitroacetophenone in a reaction system consisting essentially of water; said m-nitroacetophenone being present in the reaction system in an amount of less than about 1.66 moles per liter of water; and a catalytic amount of a nickel or palladium catalyst; said hydrogenation being carried out at a temperature of less than about 105° C and at a hydrogen pressure of 25 to about 1000 psi.

2. A process for the facile conversion of m-nitroacetophenone into m-amino-α-methylbenzyl alcohol in a single step process comprising hydrogenating m-nitroacetophenone in a reaction system consisting essentially of water; said m-nitroacetophenone being present in the reaction system in an amount less than about 1.66 moles per liter of water; and a catalytic amount of a nickel or palladium catalyst; said hydrogenation being carried out at a temperature of less than about 105° C and at a hydrogen pressure of 25 to about 110 psi.

3. The process of claim 2, wherein said temperature is between about 75° C and 105° C.

4. The process of claim 1, wherein a minor amount of acid is present in the reaction mixture when the catalyst is nickel.

5. The process of claim 1 wherein the nickel catalyst is present in an amount of from about 0.4 to about 20 parts of metal per 100 parts of m-nitroacetophenone.

6. The process of claim 1, wherein the palladium catalyst is present in an amount of from about 0.05 to about 0.25 parts of metal per 100 parts of m-nitroacetophenone.

* * * * *